(12) United States Patent
Maccagnani et al.

(10) Patent No.: US 12,287,245 B2
(45) Date of Patent: Apr. 29, 2025

(54) TIME-TEMPERATURE INDICATOR

(71) Applicants: E.O.S. S.P.A., Turin (IT); Stefano Maccagnani, Rome (IT)

(72) Inventors: Stefano Maccagnani, Rome (IT); Andrea Amato, Guidonia (IT)

(73) Assignees: E.O.S. S.P.A., Turin (IT); Stefano Maccagnani, Rome (IT)

( * ) Notice: Subject to any disclaimer, the term of this patent is extended or adjusted under 35 U.S.C. 154(b) by 442 days.

(21) Appl. No.: 17/774,494

(22) PCT Filed: Nov. 10, 2020

(86) PCT No.: PCT/IB2020/060567
§ 371 (c)(1),
(2) Date: May 5, 2022

(87) PCT Pub. No.: WO2021/094915
PCT Pub. Date: May 20, 2021

(65) Prior Publication Data
US 2022/0390289 A1  Dec. 8, 2022

(30) Foreign Application Priority Data
Nov. 12, 2019  (IT) .................. 102019000020853

(51) Int. Cl.
*G01K 3/04* (2006.01)
*G01N 31/22* (2006.01)
(Continued)

(52) U.S. Cl.
CPC .............. *G01K 3/04* (2013.01); *G01N 31/229* (2013.01); *G01N 33/02* (2013.01); *G01K 2207/04* (2013.01); *G01N 21/77* (2013.01)

(58) Field of Classification Search
CPC ..... G01K 3/04; G01K 2207/04; G01N 31/229; G01N 21/77; G01N 33/02
See application file for complete search history.

(56) References Cited

U.S. PATENT DOCUMENTS 1,540,979 A * 6/1925 Bloom ................. G01N 11/10
73/54.36
2,850,393 A * 9/1958 Romito ................ B65D 79/02
374/161
(Continued)

FOREIGN PATENT DOCUMENTS

| EP | 0577489 A1 | 1/1994 |
|---|---|---|
| KR | 20030021713 A | 3/2003 |
| WO | 2007047357 A2 | 4/2007 |

OTHER PUBLICATIONS

Search Report and Written Opinion of PCT/IB2020/060567 issued on Dec. 23, 2020.
(Continued)

*Primary Examiner* — Nathaniel T Woodward
*Assistant Examiner* — Philip L Cotey
(74) *Attorney, Agent, or Firm* — Silvia Salvadori, P.C.; Silvia Salvadori

(57) ABSTRACT

The present invention relates to a visual time-temperature indicator which comprises a first and a second element each comprising a hydrogel, wherein said first element further comprises at least one alkalinizing agent, and said second element comprising further at least one food colouring.

15 Claims, 2 Drawing Sheets

(51) Int. Cl.
 *G01N 33/02* (2006.01)
 *G01N 21/77* (2006.01)

(56) References Cited

U.S. PATENT DOCUMENTS

| | | | | |
|---|---|---|---|---|
| 2,955,942 | A * | 10/1960 | Fenity | A23B 4/08 116/201 |
| 4,022,149 | A * | 5/1977 | Berger | G01K 11/06 374/E11.006 |
| 4,753,188 | A * | 6/1988 | Schmoegner | G01K 11/06 374/E11.006 |
| 5,254,473 | A * | 10/1993 | Patel | G01N 31/229 436/1 |
| 5,667,303 | A * | 9/1997 | Arens | G01K 3/04 374/102 |
| 5,672,465 | A * | 9/1997 | Patel | G03F 7/025 430/374 |
| 6,042,264 | A * | 3/2000 | Prusik | G01K 3/04 374/150 |
| 7,036,452 | B1 * | 5/2006 | Tester | G01K 11/06 374/E11.006 |
| 9,612,162 | B2 * | 4/2017 | Røhr | G01K 3/04 |
| 2004/0222780 | A1 * | 11/2004 | Yamada | B41M 5/3375 374/E11.018 |
| 2005/0078557 | A1 * | 4/2005 | Andersen | G01N 31/229 73/29.04 |
| 2009/0010803 | A1 * | 1/2009 | Ambrozy | G01K 5/00 374/E11.006 |
| 2012/0027647 | A1 * | 2/2012 | Ambrozy | G01K 3/04 422/401 |
| 2014/0098834 | A1 * | 4/2014 | Rohr | G01K 3/04 374/102 |
| 2015/0247760 | A1 * | 9/2015 | Ambrozy | G01K 3/04 116/200 |
| 2015/0260584 | A1 * | 9/2015 | Wotzer | G01K 11/12 156/278 |
| 2015/0308901 | A1 * | 10/2015 | Salman | G01K 3/04 374/102 |
| 2016/0349224 | A1 * | 12/2016 | Patel | G07C 1/00 |
| 2017/0131152 | A1 * | 5/2017 | Wötzer | G01K 3/04 |
| 2017/0205295 | A1 * | 7/2017 | Newport | G01K 11/06 |
| 2018/0172598 | A1 * | 6/2018 | Gunasekaran | G01N 33/20 |
| 2020/0043377 | A1 * | 2/2020 | Robinson | G01N 31/229 |
| 2020/0209160 | A1 * | 7/2020 | Robinson | G09F 3/0291 |

OTHER PUBLICATIONS

Spagnuolo E., "Frozen: il sensore che ti dice se i surgelati sono stati conservati bene", calcolovotodilaurea.it, Oct. 23, 2019, pp. 1-3.

\* cited by examiner

TIME-TEMPERATURE INDICATOR

This application is a U.S. national stage of PCT/IB2020/060567 filed on 10 Nov. 2020 which claims priority to and the benefit of Italian patent application No. 102019000020853 filed on 12 Nov. 2019, the content of which are all incorporated herein by reference in their entireties.

FIELD OF THE INVENTION

The present invention relates to a visual time-temperature indicator which comprises a first and a second element, each comprising a hydrogel, wherein said first and second elements are at least partially in contact with each other.

PRIOR ART

In the food industry, the use of so-called "smart labels" grew out of the need to be able to detect any variations in the environmental conditions to which a given food is subjected and to provide the consumer with information on the possible problems connected to them.

The advantage of smart labels, compared to common sensors (which require a further device to translate the signal) resides in the fact that they are capable of detecting variations in critical parameters (e.g. time, temperature, humidity, pH, gas emission) and of giving a visual response directly, in real time.

"Shelf life" is defined as the interval of time during which a food retains an acceptable level of safety and quality and, therefore, the period of time that corresponds, under given storage conditions, to a tolerable decrease in the quality of a food. Temperature is generally the most important environmental parameter which can influence the chemical and physical deterioration of a food and/or the microbiological growth within it. For this reason there has arisen a need to develop time-temperature indicators (TTIs) that are capable not only of monitoring the shelf life of perishable products, but also of signalling any thermal abuses they may undergo in the cold chain.

Depending on their response mechanism, TTIs are generally divided into two categories: partial TTIs or total TTIs. If the visual response of the indicator comes after a given critical temperature is exceeded, they are referred to as partial TTIs; if, by contrast, they provide a continuous response, over time, regarding its thermal history, they are referred to as total TTIs.

To date, various types of TTIs have been developed; their operating principle can be based on different activation mechanisms; hence there exist indicators of a chemical, physical, biological and enzymatic type. One of the first types of chemical TTIs developed is based on a monomer which, as a result of external stimuli, undergoes an irreversible polymerization reaction leading to a change in colour of the indicator.

Another system developed instead exploits the photoactivation of an ink based on spiro-aromatic compounds; in this case the label is activated by UV radiation, which induces the appearance of a blue colour in the initially colourless ink. Due to the effect of temperature, the colour of the label will go back towards the initial stage.

TTIs of a physical type exploit a diffusion process in a dyed solution containing an ester within a porous matrix; in this case activation of the process is triggered when a specific temperature is exceeded.

Other types of smart label, by contrast, exploit enzymatic reactions, such as, for example, colour changes associated with changes in pH, due to the hydrolysis reaction between lipase and a lipid substrate.

US20090122829A1 describes the use of silver nanoparticles suitably synthesized and dispersed throughout a matrix that limits their aggregation.

However, in this case the indicator is not capable of monitoring the entire shelf life, but only reveals the possible phenomenon of thawing that a food may undergo.

U.S. Pat. No. 6,029,601A describes the change in the viscosity of a gel following a change in temperature sensed by the gel following thawing.

Although various commercial solutions have been developed, there still continue to be many drawbacks such as cost (still too high), the problem of the toxicity of some materials used and the problem of accuracy in the response.

At present, the problems of the response reliability of TTIs and the reduction of their cost per individual unit are undoubtedly the most critical areas in which there can be large room for improvement.

SUMMARY OF THE INVENTION

A first aspect of the present invention relates to a visual time-temperature indicator which comprises a first and a second element, each comprising a hydrogel, wherein said first element further comprises at least one alkalinizing agent, and said second element further comprises at least one food colouring.

A second aspect of the present invention relates to a label comprising the TTI described above; said label is preferably adhesive.

A further aspect of the present invention relates to the use of the TTI of the present invention or of the label comprising said TTI to monitor and reveal temperature changes in a perishable product, preferably foods, more preferably frozen foods.

BRIEF DESCRIPTION OF THE DRAWINGS

The present invention is described below in detail and exemplified with reference to the accompanying figures, in which.

DEFINITIONS

Figure 1:
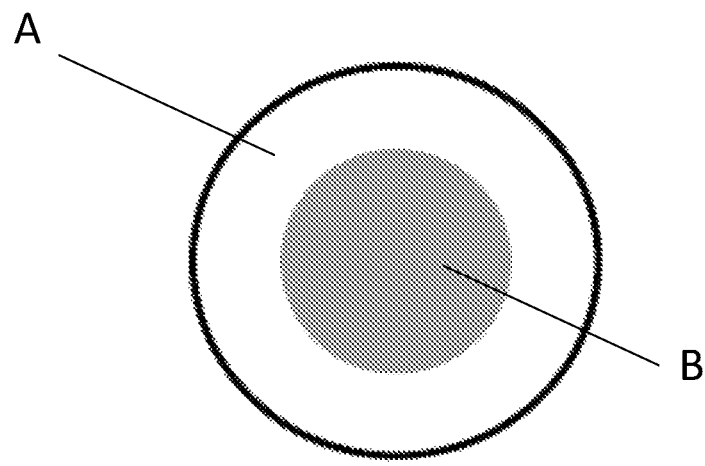
FIG. 1 shows a top view of the time-temperature indicator according to the present invention.

In the context of the present invention, "hydrogel" means a colloid formed by polymeric chains of molecules dispersed in water, whose water content can exceed 99%.

In the context of the present invention, "time-temperature indicator or TTI" means a product capable of monitoring the temperature of a material for a certain interval of time and revealing the changes thereof.

In the context of the present invention, "Bloom" means the unit of measurement referring to the resistance of a gel.

In the context of the present invention "threshold temperature" means a temperature above or below which there can be changes in the viscosity of the hydrogel.

DETAILED DESCRIPTION PREFERRED EMBODIMENTS OF THE INVENTION

A first aspect of the present invention relates to a time-temperature indicator (IIT) comprising a first and a second element, each comprising a hydrogel. Preferably, said first and said second element are at least partially in contact with each other through a contact surface.

In one embodiment, the hydrogel of each element comprises gelatine of animal or plant origin, preferably of animal origin. The gelatine preferably comprises polypeptide chains with a high molecular weight, preferably comprised between 50 kDa and 100 kDa. Said gelatine is defined, in other words, as a gelatine with a Bloom number preferably comprised between 200 and 350, more preferably comprised between 225 and 325.

In one embodiment, the first element further comprises at least one alkalinizing agent, preferably selected from: sodium carbonate, potassium bicarbonate, sodium bicarbonate, and combinations thereof. In other words, the hydrogel of the first element can also be defined as a hydrogel with an alkaline pH, for example with a pH comprised between 9 and 11.

In one embodiment, the first element is a hydrogel comprising at least one alkalinizing agent, preferably selected as described above. Said alkalinizing agent is preferably sodium carbonate.

In one embodiment, the alkalinizing agent is present in a concentration comprised between 20 and 70 mg/ml, preferably between 30 and 60 mg/ml.

In one embodiment, said second element further comprises at least one food colouring.

Said at least one colouring is preferably selected from the group consisting of: curcumin (E100), quinoline yellow (E104), riboflavin (E101), sunset yellow (E110), cochineal (E120), azorubine (E122), E131, erioglaucine (E133), indigotine (E132), E142 and combinations thereof.

Preferably, the at least one colouring is present in a concentration comprised between 1 and 7 mg/ml, preferably between 2 and 5 mg/ml.

In a preferred embodiment of the invention, the second element comprises at least two food colourings. Said at least two colourings are preferably selected in the group consisting of: curcumin (E100), quinoline yellow (E104), riboflavin (E101), sunset yellow (E110), cochineal (E120), azorubine (E122), E131, erioglaucine (E133), indigotine (E132), E142 and combinations thereof.

Said at least two colourings are preferably mixed together in order to obtain a uniform colour of the hydrogel of the second element. Said at least two colourings can be identified as the first and second colourings, wherein the first: second colouring ratio is preferably comprised between 1:250 and 1:100, preferably between 1:200 and 1:130.

In a preferred embodiment of the invention, said at least two colourings are curcumin and erioglaucine (E133).

In one embodiment, the second element further comprises at least one plasticising agent.

Preferably, said plasticising agent is selected from: glycerol, hydrogenated or partially hydrogenated vegetable oil, cocoa butter, sorbitol or other polyols, glycerine, polyethylene glycols, propylene glycol, corn syrup, lecithin, hydrogenated lecithin, mono-, di- and triglycerides, acetylated monoglycerides, stearic, palmitic, oleic and linoleic acids and combinations thereof. In a preferred embodiment of the invention, said plasticiser is selected from glycerol, polyethylene glycols and combinations thereof.

Preferably, said plasticising agent is present in a concentration comprised between 15 and 80 mg/ml, preferably between 20 and 70 mg/ml.

In one embodiment, the second element is a hydrogel comprising at least one food colouring and at least one plasticising agent.

In one embodiment, said first and second elements are prepared separately and the TTI is assembled afterwards. One proceeds by preparing the hydrogel, which is the base common to both elements, and then adds the specific compounds for the preparation of the first or second element.

Preferably, the hydrogel is prepared by mixing gelatine with water, for example, at a temperature comprised between 20 and 50° C. until the gelatine has solubilized. The gelatine is present in a final concentration comprised between 140 and 180 mg/ml, preferably between 150 and 170 mg/ml.

For the preparation of the first element, at least one alkalinizing agent selected from the ones listed previously is added to the gelatine solution described above.

Once completely solubilized, the solution obtained is poured into a mould to allow it to cool and to obtain the first element with the desired shape.

The first element is preferably poured into a mould comprising a hollow perimeter region, adapted to enable the distribution of the solution, and a central region that is raised relative to the perimeter region, adapted to prevent the distribution of the solution. The first element thus obtained is therefore defined by the shape of the perimeter region of the mould, i.e. a contour, at the centre of which an empty portion is identified.

The second element is preferably prepared by mixing the at least one colouring with the at least one plasticiser. The mixture obtained is then placed under stirring, preferably at a temperature comprised between 25 and 55° C., more preferably between 30 and 50° C.

The solution comprising the colouring is then added to the solution comprising gelatine described above and placed under stirring, preferably at a temperature comprised between 25 is 55° C., more preferably between 30 and 50° C.

Once completely solubilized, the solution obtained is poured into a mould to allow it to cool and to obtain the second element with the desired shape. Preferably, the second element has a shape that allows it to be housed in the first element, preferably in the empty portion of the first element. In other words, the second element is surrounded by the first element and said elements are at least partially a contact with each other through a contact surface.

In an alternative embodiment of the invention, the respective positions of the first and second elements can be inverted, i.e. the second element, comprising the at least one colouring, is placed on the outside so as to surround the first element, comprising the at least one alkalinizing agent.

In a preferred embodiment of the invention, the TTI comprises the first element, preferably circular in shape, which completely surrounds the second element, which is likewise circular in shape. Said first element and said second element are at least partially in contact with each other through a contact surface. Therefore, the first element and the second element, in a top view of the TTI, appear as two concentric circles, said first element being the outer circle A and said second element being the inner circle B, as shown in FIG. 1. In this embodiment the first element is definable as a support and the second element as a detector.

The TTI according to the present invention is suitable for monitoring and revealing changes in the temperature of perishable products, preferably foods, more preferably frozen foods. In fact, the TTI is preferably applied directly on a perishable product, more preferably on packaging that is directly in contact with the perishable product.

In one embodiment, the exceeding of a temperature threshold of the perishable product causes the diffusion of the hydrogel of the first element into the hydrogel of the second element. In particular, corresponding with a rise in the temperature of the perishable product there is a release of an aqueous portion of the hydrogel of the first element, which migrates towards the second element. The migration of the aqueous portion of the first element into the second element is apt to cause a progressive and irreversible change in colour of the second element. In other words, the TTI is capable of monitoring and revealing changes in the temperature of the perishable product beyond a predetermined temperature threshold value. For example, the TTI of the present invention is suitable for monitoring and revealing changes in the temperature of a frozen product which could cause a deterioration of the product itself.

In a preferred embodiment of the invention, the threshold temperature is comprised between −25° C. and −20° C., preferably between −22° C. and −20° C.

A colour that is unchanged from the initial colour of the second element, which, for example is green, indicates that the perishable product has remained uninterruptedly below the established threshold temperature, for example below −20° C. "Initial colour" of the second element means the colour of the second element imparted by the at least one colouring according to the invention. An unchanged colour is shown, for example, in FIG. 2a.

The change in colour of the second element begins when the threshold temperature is exceeded, that is, when the perishable product reaches a temperature comprised between −20° C. and −18° C.

In this case, the change in colour involves the perimeter of the second element, for example, the colour of the perimeter of the second element turns from green to orange. Said colour of the second element indicates that the frozen product has been exposed to a temperature higher than the established threshold temperature, but the product has not undergone a deterioration requiring it not to be placed on the market or to be withdrawn therefrom. FIG. 2b shows an example of this change in colour, where only the perimeter of the second element has changed.

If the temperature of the perishable product is comprised between −18° C. and −15° C., the change in colour will occur in the whole area of the second element, for example, the colour of the second element will turn from green to orange. In this case as well, the colour of the second element indicates that the frozen product has been exposed to a temperature higher than the established threshold temperature, but the product has not undergone a deterioration requiring it not to be placed on the market or to be withdrawn therefrom (FIGS. 2c and 2d).

If, on the other hand, the temperature of the perishable product exceeds −15° C., there will be a further change in colour of the second element, for example, towards a darker shade compared to the colour taken on previously; for example, the colour of the second element will turn from orange to red. The exceeding of the threshold value of −15° C., together with the darker colour of the second element, for example red, indicates that the frozen product has undergone deterioration and cannot be placed on the market or must be withdrawn from the market (FIG. 2e).

If the temperature of the perishable product is brought back down to a temperature lower than the threshold temperature, the colour reached by the second element will not change any further; in fact, the progressive changes in colour of the second element are not reversible.

The threshold temperature values may vary according to the nature of the perishable product and the method of transport and/or storage thereof. Advantageously, the Applicant has demonstrated that the TTI of the present invention is capable of monitoring and revealing changes in the temperature of perishable products. Unlike other TT's present on the market, the TTI of the present invention enables changes in temperature to be irreversibly displayed, thereby preventing possible food fraud. In this respect, the TTI of the present invention is capable of "recording" the thermal history of the product, that is, of permanently indicating whether a temperature threshold value has been exceeded or the product has deteriorated. Moreover, the TTI of the present invention comprises materials that are compatible with the production of foods and nontoxic and have a relatively low cost.

A second aspect of the present invention relates to a label comprising the TTI described above. Preferably, said label is adhesive. In this manner, the TTI of the present invention can be positioned on a perishable product, preferably on packaging of a perishable product, more preferably on packaging directly in contact with a perishable product.

Said label comprises a background, preferably light-coloured, for example white, on top of which the TTI of the present invention is positioned, so as to enable an easy reading of the TTI and an easy identification of changes in the colour of the second element.

A further aspect of the present invention relates to the use of the TTI or of the label comprising said TTI as described above in detail to monitor and reveal changes in the temperature of a perishable product, preferably foods, more preferably frozen foods. In one embodiment of the invention, the TTI is positioned on a perishable product, preferably on packaging of a perishable product, more preferably on packaging directly in contact with a perishable product.

Example

The time-temperature indicator (TTI) was made using an animal gelatine (Type A—300 g Bloom), which formed the matrix for both components (first and second elements) of the TTI itself. The stock solution of gelatine from which said components are derived has a concentration of 160 mg/ml; this concentration, associated with the high Bloom value, enables easily processable objects to be obtained.

The solvent used for the preparations is distilled water. The gel of the first element contains high-purity $Na_2CO_3$—sodium carbonate at a concentration of 50 mg/ml, whereas the gel with which the second element is made contains the chemical species listed in Table 1 (the concentrations used are indicated).

TABLE 1 name and concentration of the chemical species of the second element

| Chemical species | Concentration [mg/ml] |
|---|---|
| Curcumin | 3 |
| Erioglaucine (or E133) | 0.02 |
| Glycerol (or glycerine) | 40 |
| Polyethylene glycol 400 (or PEG-400) | 20 |

In addition to the aforementioned properties, the Type A animal gelatine—300 g Bloom was selected as it is able to provide a better incorporation of the curcumin than Type B animal gelatine.

Again with respect to the second element, glycerol and Peg-400 enable the solubility of the curcumin in the aqueous environment to be further increased and, being compounds with a plasticising action, these chemical species make it possible to vary the colouring times of the second element according to the concentration used.

The initial green colour of the latter was obtained simply by adding a blue food colouring: Erioglaucine, also identified by the code E133 (E number). This colouring, in combination with curcumin (yellow in colour), imparts a final green colour to the gels.

Since the temperature influences the diffusion phenomena that occur inside the gelatinous matrix, the exposure of the invention to room temperature will cause a progressive diffusion of the base contained in the first element towards the curcumin, with a consequent change from the initial colour. The appearance of a rust colour will indicate that the temperature limit imposed by current regulations has been exceeded. The development of a red colour will instead be correlated to a thermal abuse of a greater entity (>−5° C.).

Once the two elements have been stored overnight at −30° C., the second element is inserted in the housing of the first element. The object thus obtained is vacuum packed and then stored at −30° C.

Preparation of the First Element 800 mg of animal gelatine are weighed in a 25 ml beaker (Type A—Sigma Aldrich); 5 ml of a standard solution of sodium carbonate are then added at a concentration of 50 mg/ml. The mixture thus obtained, at a concentration of 160 mg/ml in gelatine, is placed under stirring at 300 rpm at a temperature of 40° C. until complete solubilization of the gelatine.

Figure 2:
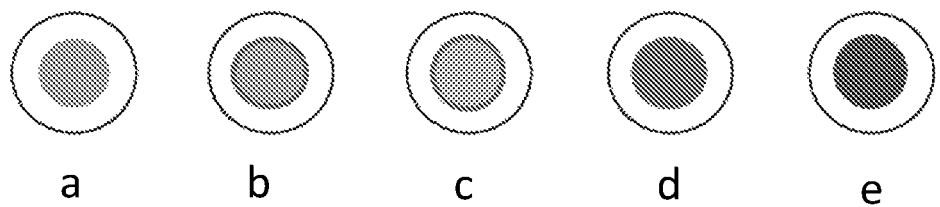
FIG. 2 shows the colour changes of the time-temperature indicator of the present invention.
Figure 3:
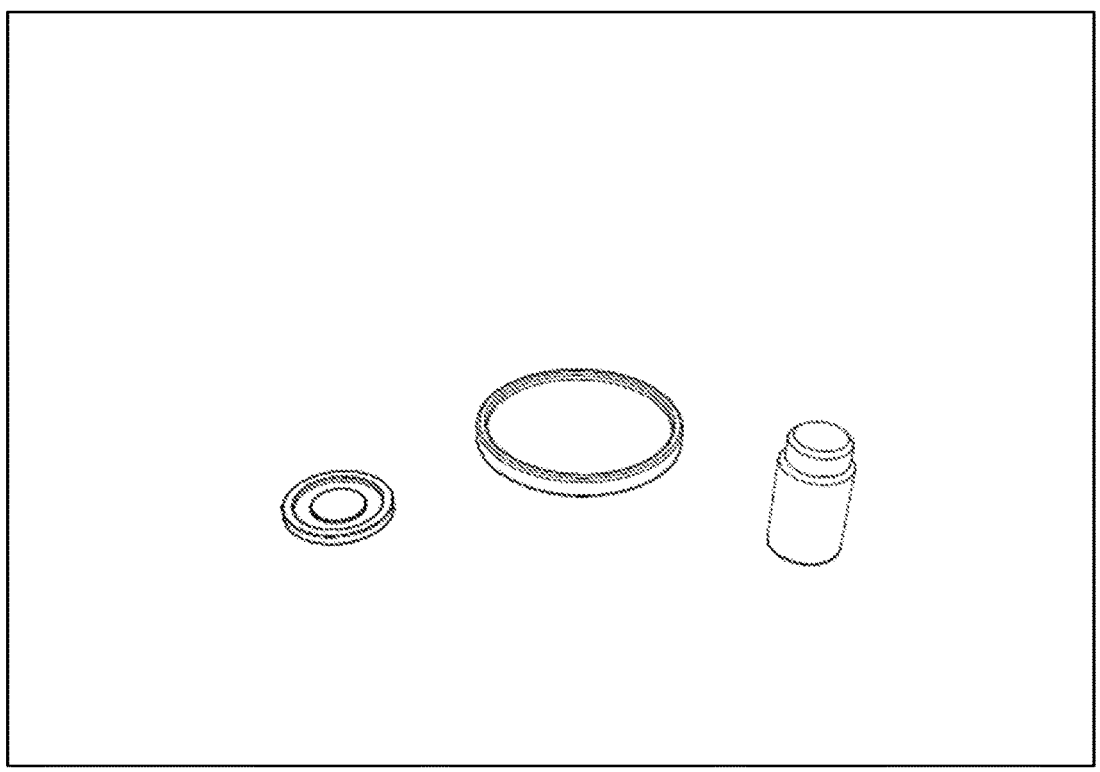
FIG. 3 shows the moulds used to prepare the elements of the TTI; Left: Teflon mould for producing the first element—Centre: stainless steel mould used to produce the gel of the second element—Right: stainless steel hollow cutter used to cut the second element.

At the end of this operation, 280 µL of the mixture obtained are added in a Teflon mould shown in FIG. 2 (taking care to completely fill the mould). Depending on the amounts used, it is possible to fill about 15 moulds; the latter, once filled, are stored in a refrigerator for 30 minutes so as to cool the gel and ensure that it has a compact structure and is easy to handle. The first element thus obtained, once removed from the mould, is stored overnight at −30° C.

Preparation of the Second Element 15 mg of curcumin is weighed in a 25 ml beaker; curcumin extracted from *Curcuma Longa* (Sigma-Aldrich) was used for these experiments. 160 µL of glycerol and 90 µL of Peg-400 (Alfa-Aesar) are then added.

The mixture is placed under stirring for 30 minutes at 45° C. It is then brought to a volume of 5 ml with a solution of animal gelatine (Type A) at a concentration of 160 mg/ml; the mixture thus obtained is placed under stirring at 300 rpm at a temperature of 45° C. until complete homogenization of the mixture itself.

250 µL of a 500 µM solution of erioglaucine were then added in aliquots of 50 µL, waiting for the mixture to homogenize after every addition; the mixture, now green in colour, is left under stirring for 30 minutes.

At the end of this operation, the circular steel mould (shown in FIG. 2) is slightly heated and 1.8 g of the mix just prepared are poured onto it.

The gel is kept in a refrigerator for 30 minutes in order to make it easier to work with.

Then, once cooled, it can be cut with the steel hollow cutter so as to obtain 7-8 second elements from each mould (see FIG. 2)

Assembly and Packaging of the TTI

The second element is inserted into the housing of the first element and the TTI thus assembled is inserted into a transparent plastic pouch and vacuum packed. This operation must be carried out rapidly in order to prevent a premature activation of the device which, at the end of the packaging operation, is stored at −30° C.

Assessment of the Functionality of the TTI

The TTI prototype made was tested on frozen foods in a bag, in this case Piselli Finissimi Freshona (baby peas).

The test was carried out by applying the TTI on the outer packaging of the food and taking care to apply it in an area in direct contact with the mass of the frozen product (applying it in an air-filled area of the package would give an unreliable response, since it would react much more rapidly than it should—tests in which the area of application of the TTI is different from the one just described will be conducted in the future).

The temperature measurements were made by means of an RS Pro-Mote-DTP+two-channel data logger; the probes of the device are inserted into the heart of the product, penetrating the latter at a depth of at least 2 cm from the surface and below the applied THI. Moreover, the probes are inserted while the product is still inside the freezer, waiting until the temperature reaches a constant value.

In addition to these measurements, the colorimetric changes of the TTI were recorded during the defrost procedure by means of a PCE-CSM 4 colorimeter. The recording of the colorimetric changes of the second element takes place immediately after the removal of the product from the freezer (time zero), and thereafter every 120 seconds.

By performing the measurements at such time intervals, one obtains a considerable number of measurements while avoiding excessively disturbing the system.

In general, starting from an initial internal temperature of the product of about −30° C., one observes a final "rust" colour of the TTI at the moment when the internal temperature reaches a value of about −10° C. (average of 10 temperature measurements); this colour is reached in a completely gradual manner.

From the analysis of the colorimetric data it emerges that a small increase in the value of H* (i.e. the colour perceived by the colorimeter) occurs immediately after the product's removal from the freezer; this phenomenon is ascribable to the "thermal shock" to which the TTI is subjected upon exposure to a temperature that is much higher than the one it was exposed to before (the measurements are performed at a temperature of 25° C.). The resulting thermal shock could lead to dimensional changes affecting the second element, with a consequent change in the colorimetric parameters.

Figure 4:
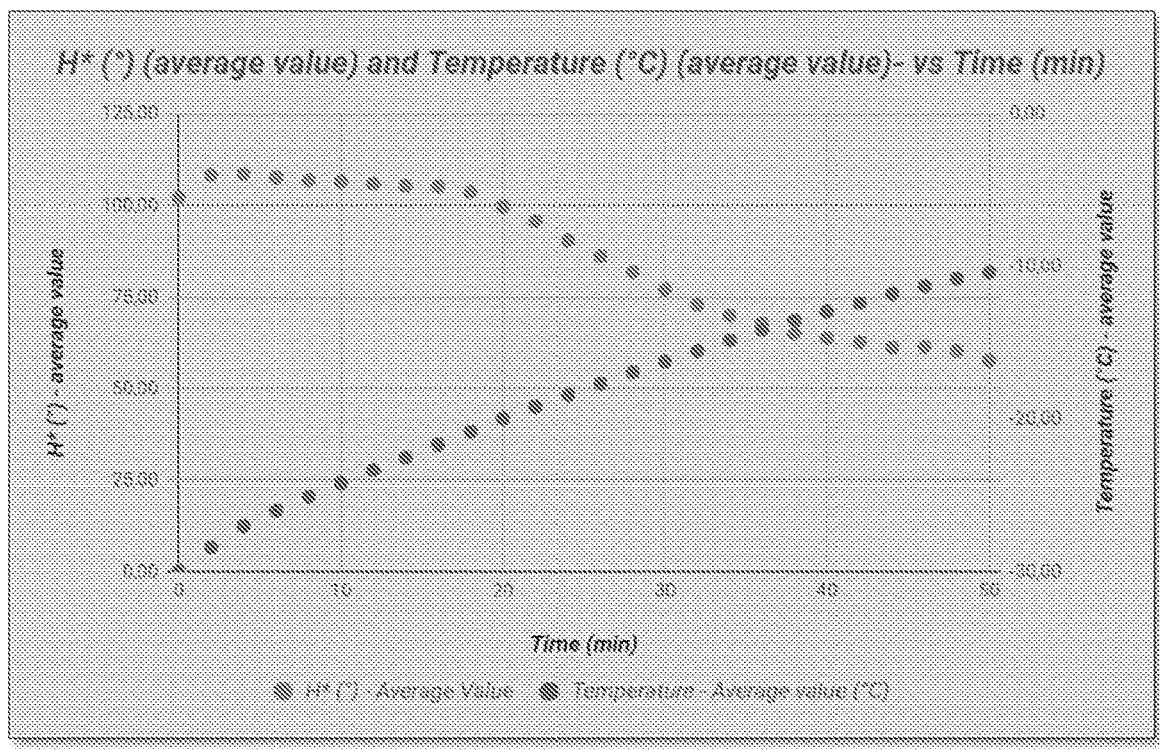
FIG. 4 shows the time-temperature graph for the parameter H*.

From a visual/colorimetric viewpoint, the phase in which one observes the formation of a red crown along the perimeter of the second element (see FIG. 1) always occurs 16-18 minutes after the start of the test; after this interval of time, one observes a progressive decrease in the parameter H* (FIG. 4).

In particular, between 22 and 24 minutes, when the parameter H* takes on values comprised between 95 and 90 degrees, the TTI undergoes an "activation", i.e. the actual diffusion process begins within it; during this process the second element takes on a less vivid colour tending towards orange. Under these conditions, the internal temperature of the product is comprised between −19 and −18° C.

Then a progressive colouring of the second element takes place, as it turns towards a rust colour when the internal temperature reaches −10° C.; in the case of the product tested in these experiments, this condition is reached in 50 minutes with an external temperature of 25° C.

The invention claimed is:

1. A visual time-temperature indicator which comprises a first and a second element each comprising a hydrogel, wherein said first element further comprises at least one alkalinizing agent and said second element further comprising at least one food colouring, wherein said first and second elements are at least partially in contact with each other through a contact surface, wherein each hydrogel comprises a gelatine of animal or plant origin with a Bloom number comprised between 200 and 350.

2. The indicator according to claim 1, wherein the at least one alkalinizing agent is selected from: sodium carbonate, potassium bicarbonate, sodium bicarbonate, and combinations thereof.

3. The indicator according to claim 1, wherein the at least one food colouring is selected from: curcumin (E100), quinoline yellow (E104), riboflavin (E101), sunset yellow (E110), cochineal (E120), azorubine (E122), E131, erioglaucine (E133), indigotine (E132), E142 and combinations thereof.

4. The indicator according to claim 1, wherein the second element comprises at least two colourings.

5. The indicator according to claim 4, wherein the second element comprises curcumin (E100) and erioglaucine (E133).

6. The indicator according to claim 1, wherein the second element further comprises at least one plasticising agent.

7. The indicator according to claim 6, wherein said at least one plasticising agent is selected from the group consisting of glycerol, hydrogenated or partially hydrogenated vegetable oil, cocoa butter, sorbitol or other polyols, glycerine, polyethylene glycols, propylene glycol, corn syrup, lecithin, hydrogenated lecithin, mono-, di- and triglycerides, acetylated monoglycerides, stearic, palmitic, oleic and linoleic acids and combinations thereof.

8. The indicator according to claim 1, wherein the second element is housed in a space identified by the first element.

9. The indicator according to claim 1, wherein said first and said second elements are circular in shape.

10. The indicator according to claim 9, wherein said second element surrounds said first element.

11. A label comprising the visual time-temperature indicator according to claim 1, wherein said label is an adhesive label.

12. A method of monitoring and detecting-variations in temperature of a perishable product with the visual time-temperature indicator according to claim 1, said method comprising
verifying changes of colour of the second element of the visual time-temperature indicator.

13. The method according to claim 12, wherein said perishable product is food.

14. The method according to claim 12, wherein said perishable product is frozen food.

15. The visual time-temperature indicator according to claim 1, wherein each hydrogel comprises a gelatine of animal or plant origin with a Bloom number comprised between 225 and 325.

* * * * *